United States Patent
Zeng

(10) Patent No.: US 10,723,811 B2
(45) Date of Patent: Jul. 28, 2020

(54) HOMOGENEOUS POLYSACCHARIDE WITH IMMUNOREGULATION ACTIVITY AND PREPARATION METHOD THEREOF

(71) Applicant: Second Affiliated Hospital of Guangzhou University of Traditional Chinese Medicine, Guangzhou, Guangdong (CN)

(72) Inventor: Xing Zeng, Guangdong (CN)

(73) Assignee: Second Affiliated Hospital of Guangzhou University of Traditional Chinese Medicine, Guangzhou (CN)

( * ) Notice: Subject to any disclaimer, the term of this patent is extended or adjusted under 35 U.S.C. 154(b) by 101 days.

(21) Appl. No.: 15/943,701

(22) Filed: Apr. 3, 2018

(65) Prior Publication Data

US 2019/0077886 A1  Mar. 14, 2019

Related U.S. Application Data

(63) Continuation of application No. PCT/CN2018/075902, filed on Feb. 9, 2018.

(30) Foreign Application Priority Data

Sep. 12, 2017 (CN) .......................... 2017 1 0817533

(51) Int. Cl.
| | |
|---|---|
| C08B 37/00 | (2006.01) |
| C13K 13/00 | (2006.01) |
| A61P 37/04 | (2006.01) |
| A61K 31/716 | (2006.01) |

(52) U.S. Cl.
CPC ........ *C08B 37/0009* (2013.01); *A61K 31/716* (2013.01); *A61P 37/04* (2018.01); *C08B 37/0003* (2013.01); *C13K 13/007* (2013.01); *C07B 2200/07* (2013.01)

(58) Field of Classification Search
None
See application file for complete search history.

(56) References Cited

PUBLICATIONS

Tian, C. C., Zha, X. Q., Pan, L. H., & Luo, J. P. (2013). Structural characterization and antioxidant activity of a low-molecular polysaccharide from Dendrobium huoshanense. Fitoterapia, 91, 247-255. (Year: 2013).*

Pang, X., Chen, Z., Gao, X., Liu, W., Slavin, M., Yao, W., & Yu, L. L. (2007). Potential of a novel polysaccharide preparation (GLPP) from Anhui-Grown Ganoderma lucidum in tumor treatment and immunostimulation. Journal of food science, 72(6), S435-S442. (Year: 2007).*

Sotome, K., Hattori, T., Ota, Y., To-anun, C., Salleh, B., & Kakishima, M. (2008). Phylogenetic relationships of Polyporus and morphologically allied genera1. Mycologia, 100(4), 603-615. (Year: 2008).*

Sun, Y., & Zhou, X. (2014). Purification, initial characterization and immune activities of polysaccharides from the fungus, *Polyporus umbellatus*. Food Science and Human Wellness, 3(2), 73-78. (Year: 2014).*

Li, X., & Xu, W. (2011). TLR4-mediated activation of macrophages by the polysaccharide fraction from Polyporus umbellatus (pers.) Fries. Journal of ethnopharmacology, 135(1), 1-6. (Year: 2011).*

He, P. F., He, L., Zhang, A. Q., Wang, X. L., Qu, L., & Sun, P. L. (2017, online Aug. 2016). Structure and chain conformation of a neutral polysaccharide from sclerotia of *Polyporus umbellatus* . Carbohydrate polymers, 155, 61-67. (Year: 2016).*

* cited by examiner

*Primary Examiner* — Dale R Miller
(74) *Attorney, Agent, or Firm* — Wayne & Ken, LLC; Tony Hom

(57) ABSTRACT

The present invention relates to a homogeneous polysaccharide with an immunoregulation activity and a preparation method thereof. The homogeneous polysaccharide with the immunoregulation activity is a single chromatographic peak and has a molecular weight of 6880±50 Da and an optical rotation value of 158.4±0.5°. An infrared spectrum has an α-configuration sugar characteristic absorption peak at 847.6 cm$^{-1}$. Hydrogen-proton characteristic chemical shifts in hydrogen spectra of the polysaccharide are δ 5.40, 3.95, 3.84 and 3.61. Carbon signal characteristic chemical shifts in carbon spectra are δ 99.6, 76.6, 73.3, 71.5, 71.1 and 60.4. The homogeneous polysaccharide has an effect of enhancing body immunity, can achieve excellent anti-tumor, antiviral and anti-infection effects and the like in regulation of immunity-related diseases, and has potential development values in drug and health care product industries for treatment and prevention of the diseases.

6 Claims, 16 Drawing Sheets

Specification includes a Sequence Listing.

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
tactcggcaa acctagtgcg                                              20

<210> SEQ ID NO 2
<211> LENGTH: 25
<212> TYPE: DNA
<213> ORGANISM: Artificial Sequence
<220> FEATURE:
<223> OTHER INFORMATION: synthetic

```
<400> SEQUENCE: 2
gtgtcccaac attcatattg tcagt                                          25

<210> SEQ ID NO 3
<211> LENGTH: 20
<212> TYPE: DNA
<213> ORGANISM: artificial sequence
<220> FEATURE:
<223> OTHER INFORMATION: synthetic

<400> SEQUENCE: 3
cggcaaacat gacttcaggc                                                20

<210> SEQ ID NO 4
<211> LENGTH: 20
<212> TYPE: DNA
<213> ORGANISM: artificial sequence
<220> FEATURE:
<223> OTHER INFORMATION: synthetic

<400> SEQUENCE: 4
gcacatcaaa gcggccatag                                                20

<210> SEQ ID NO 5
<211> LENGTH: 20
<212> TYPE: DNA
<213> ORGANISM: artificial sequence
<220> FEATURE:
<223> OTHER INFORMATION: synthetic

<400> SEQUENCE: 5
ggggattatg gctcagggtc                                                20

<210> SEQ ID NO 6
<211> LENGTH: 20
<212> TYPE: DNA
<213> ORGANISM: artificial sequence
<220> FEATURE:
<223> OTHER INFORMATION: synthetic

<400> SEQUENCE: 6
cgaggctcca gtgaattcgg                                                20

<210> SEQ ID NO 7
<211> LENGTH: 21
<212> TYPE: DNA
<213> ORGANISM: artificial sequence
<220> FEATURE:
<223> OTHER INFORMATION: synthetic

<400> SEQUENCE: 7
ccatggaatc cgtgtcttcc t                                              21

<210> SEQ ID NO 8
<211> LENGTH: 20
<212> TYPE: DNA
<213> ORGANISM: artificial sequence
<220> FEATURE:
<223> OTHER INFORMATION: synthetic

<400> SEQUENCE: 8
gtcttggccg aggactaagg                                                20

<210> SEQ ID NO 9
```

```
<211> LENGTH: 25
<212> TYPE: DNA
<213> ORGANISM: artificial sequence
<220> FEATURE:
<223> OTHER INFORMATION: synthetic

<400> SEQUENCE: 9
tttgtcaagc tcatttcctg gtatg                                         25

<210> SEQ ID NO 10
<211> LENGTH: 18
<212> TYPE: DNA
<213> ORGANISM: artificial sequence
<220> FEATURE:
<223> OTHER INFORMATION: synthetic

<400> SEQUENCE: 10
tgggataggg cctcttgc                                                 18
```

HOMOGENEOUS POLYSACCHARIDE WITH IMMUNOREGULATION ACTIVITY AND PREPARATION METHOD THEREOF

REFERENCE TO AN ELECTRONIC SEQUENCE LISTING

The contents of the electronic sequence listing (15943701SequenceListing.txt; Size: 2,000 bytes; and Date of Creation: Apr. 30, 2018) is herein incorporated by reference in its entirety.

TECHNICAL FIELD

The present invention relates to the technical field of homogeneous polysaccharides, and particularly relates to a homogeneous polysaccharide with an immunoregulation activity and a preparation method thereof.

BACKGROUND

Some traditional Chinese medicine polysaccharides have effects of activating immune cells, improving body immunity functions and the like, and bring attentions of researchers by virtue of the advantages of exact effects, small toxic and side effects and the like. The traditional Chinese medicine polysaccharides serve as immunoregulators with developing potential and will achieve significant effects in the processes of eliminating diseases and enhancing human resistance. However, at present, the study on most of the traditional Chinese medicine polysaccharides is limited to total polysaccharides, and the study on specific molecular compositions and action mechanisms of the polysaccharides is unclear. Therefore, substance structures of the traditional Chinese medicine polysaccharides and effects and mechanisms thereof on an immune system are intensively and systematically researched, and pharmacodynamic substances of the traditional Chinese medicine polysaccharides are expected to be recognized from a deeper level.

*Polyporus* polysaccharide is a main active ingredient in a water extract of a traditional Chinese medicine *polyporus*, is a good immunoregulator and has effects of resisting tumors, performing immunoregulation, protecting liver, and resisting oxidation, radiation and mutagenesis, and the like. Preliminary study of the present study discovers that *Polyporus umbellatus* fries has an excellent effect of preventing BBN-induced bladder carcinoma and also has an effect of obviously increasing an immunologic function thereof. Correlational studies are also made on immunomodulatory effects and mechanisms of the *Polyporus umbellatus* fries, while the objects of the above studies are the *Polyporus umbellatus* fries, not involving any specific ingredient and an immunity-associated activity thereof in the *Polyporus* polysaccharide. However, with respect to component study on the *Polyporus* polysaccharide, Japanese scholars report that the *Polyporus* contains a water-soluble polyglucan 6-branched-β-1, 3-glucan, a monosaccharide composition is glucose only, and all components are of a β-configuration. It is also reported that, a homogeneous polysaccharide which has a molecular weight of about 2.27 million and mainly contains D-glucose, a homogeneous polysaccharide which has a molecular weight of 14000 and contains glucose and glucuronic acid and a homogeneous polysaccharide which has a molecular weight of about 8800 and contains glucuronic acid are separated from the *Polyporus*.

A simple and effective polysaccharide extraction process and method are adopted in the present study. A novel *Polyporus* polysaccharide (PPS) different from that reported in an existing literature is separated and identified from the *Polyporus* medicinal material for the first time. It is proved that, the PPS has the monosaccharide composition of the glucose only and also has an α-configuration and a main connection manner of 1→4. Anti-tumor immunoregulatory activities and action mechanisms of the PPS are researched. It is first discovered that, the PPS has excellent immunoregulation and treatment effects, and has potential prevention and health effects on diseases.

SUMMARY

A technical problem to be solved in the present invention is as follows: in order to solve the problems in the prior art in the above background, the present invention provides a homogeneous polysaccharide with an immunoregulation activity and a preparation method thereof. The homogeneous polysaccharide has an effect of enhancing body immunity, can achieve excellent anti-tumor, antiviral and anti-infection effects and the like in regulations and summarization of immunity-related diseases, and has potential development values in drug and health care product industries for treatment and prevention of the diseases.

A technical solution adopted to solve the technical problem in the present invention is as follows: the polysaccharide composition with the immunoregulation activity is a single chromatographic peak and has a molecular weight of 6880±50 Da and an optical rotation value of 158.4±0.5°. An infrared spectrum has a characteristic absorption peak at 847.6 cm-1. Hydrogen-proton characteristic chemical shifts in hydrogen spectra of the polysaccharide are δ5.40 brs, 3.95 t, J=7.2 Hz, 3.84 m and 3.61 m. Carbon signal characteristic chemical shifts in carbon spectra are δ99.6, δ76.6, δ73.3, δ71.5, δ71.1 and δ60.4.

Further specifically, in the above technical solution, a mass content of the polysaccharide in the polysaccharide composition is 92-98%; Agilent1200 liquid chromatography is adopted, a refractive index detector RID is used for analyzing, a chromatographic column is TSK-GEL G4000 PW×L, a mobile phase is ultrapure water, a flow velocity is 0.3-1 ml/min, a detector temperature is 30-40° C., a column temperature is 30-50° C., chromatographic analysis is made by a single peak, and retention time is 10-30 min.

Further specifically, in the above technical solution, the polysaccharide is singly composed of α-D-glucopyranosyl, and the polysaccharide has an α-configuration and a connection manner of 1→4.

Further specifically, in the above technical solution, the polysaccharide composition further comprises one of a fluorescence labeled product, a carboxymethylation product, a hydroxymethylation product, a hydroxypropylation product, an ethylene glycol product, a propylene glycol product and a polyethylene glycol product.

A preparation method of the polysaccharide composition with the immunoregulation activity includes the following steps:

step 1: performing water heating and extraction, and performing alcohol precipitation to prepare total polysaccharides;

grinding *Polyporus umbellatus* Fries, adding 3 L of deionized water into 300 g of the ground *Polyporus umbellatus* Fries, soaking at room temperature for 1 hour, and heating at 100° C. and performing reflux extraction twice, extracting for 1 h each time, filtering, merging filtrates, concentrating to 600 ml, centrifuging at 3000 rpm for 10 min, regulating an ethanol ratio in a supernatant to be greater than 80%, standing overnight at 4° C., filtering the supernatant, precipitating and performing freeze-drying to obtain a crude polysaccharide, adding purified water into the crude polysaccharide to prepare a solution of 25-35 mg·mL$^{-1}$;

step 2: removing crude polysaccharide protein;

preparing sugar liquor, chloroform and n-butyl alcohol according to a ratio of 25:4:1, pouring the above components into a separating funnel, fully shaking for 3 min, standing, layering, removing an organic layer and precipitates, repeatedly removing the protein until a white precipitate is not produced, collecting the supernatant, concentrating to an appropriate volume by using a rotary evaporator, transferring, and performing freeze-drying to obtain a crude polysaccharide without the protein;

step 3: performing depigmentation by DEAE-52 cellulose;

respectively adding a small amount of water into the crude polysaccharides without proteins and dissolving, discoloring using a pretreated DEAE-52 cellulose column of 35×3 cm, eluting with 1 mL/min of ultrapure water and 0.1-0.5% of sodium chloride solution, eluting until any sugar is not detected in effluent by using a phenol-dense sulfuric acid method, collecting the eluant on a peak section, concentrating by using the rotary evaporator, performing freeze-drying, and desalting to obtain a white loose powdered pure polysaccharide; and step 4: refining by a Sephadex G-100 gel column;

dissolving an appropriate amount of the pure polysaccharide into distilled water, adding the Sephadex G-100 gel column, eluting with pure water and 0.1-0.5% of sodium chloride solution, controlling flow velocity to 1 ml/min, collecting every 10 mL of the eluant into a tube, and tracking and monitoring by the phenol-dense sulfuric acid method; taking numbers of detection tubes as a horizontal coordinate and taking optical density as a vertical coordinate to draw a polysaccharide elution curve, collecting the eluant on the peak section, performing freeze-drying, and desalting to obtain the homogeneous polysaccharide.

Further specifically, in the above technical solution, a pretreatment method of the DEAE-52 cellulose column in the step 3 includes the following steps:

step 1: soaking the cellulose of dried powder in distilled water for 2-5 h, removing impurities and then draining;

step 2: soaking with a 0.5 mol/L of HCL solution for 1-3 h, washing with deionized water, regulating a pH to be neutral, and draining; and step 3: soaking the drained cellulose in a 0.5 mol/L of NaOH solution for 1-3 h, washing with the deionized water, regulating the pH to be neutral, and draining.

The present invention has beneficial effects as follows: the homogeneous polysaccharide has the effect of enhancing the body immunity, can achieve excellent anti-tumor, antiviral and anti-infection effects and the like in regulations and summarization of the immunity-related diseases, and has potential development values in drug and health care product industries for treatment and prevention of the diseases.

BRIEF DESCRIPTION OF DRAWINGS

The present invention is further described below in combination with drawings and embodiments.

DETAILED DESCRIPTION

Figure 1:
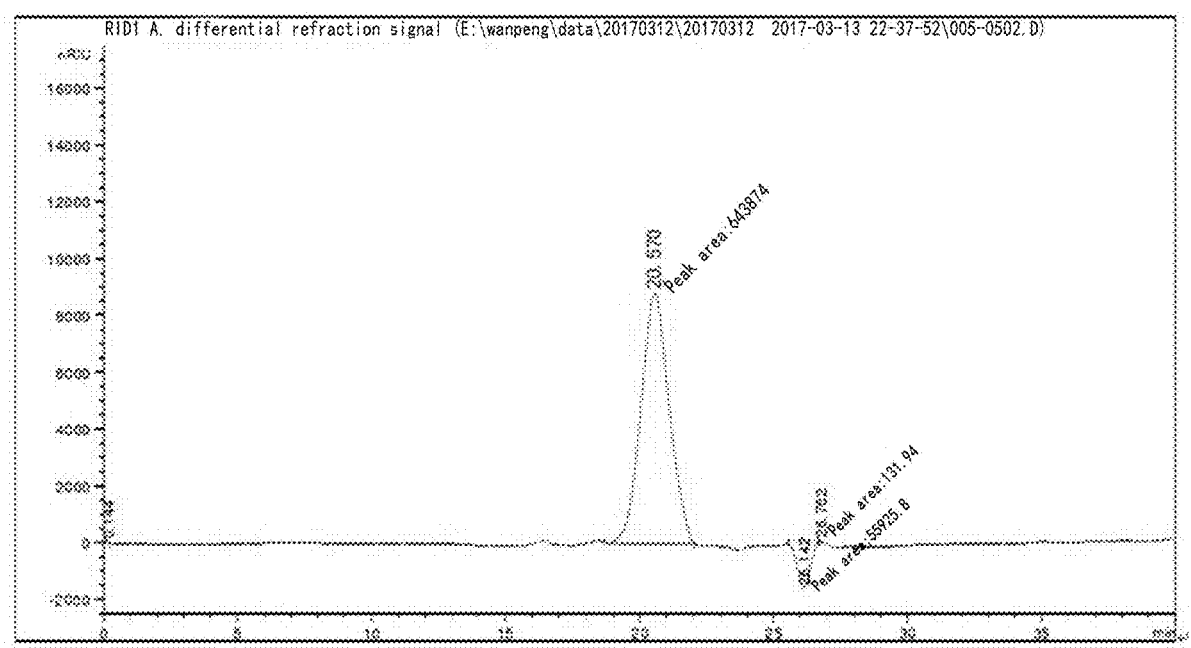
FIG. 1 is a chromatogram map of a *Polyporus umbellatus* Fries polysaccharide PPS HPLC-RID.

The present invention is further described in detail in combination with drawings. These drawings are simplified schematic diagrams. A basic structure of the present invention is described in a schematic manner only. Therefore, a composition related to the present invention is shown only.

In the present application, the polysaccharide composition may be extracted from the *Polyporus umbellatus* Fries, may also be separated from other fungi and plants, or can be obtained by microbial fermentation, artificial synthesis and other means as long as the homogeneous polysaccharide has the molecular weight and physic-chemical spectral characteristics. Achieved effects include effects of obviously promoting NO secretion of macrophage, obviously increasing expressions of macrophages of IL-1β, IL-6 and TNF-α as well as genes of iNOS and proteins of iNOS and COX-2 and increasing expressions of macrophage membrane surface receptors of CD11b, CD16/32, CD40, CD14, CD284 and CD282 as well as expressions of P-P38 and P-P65 protein tyrosine phosphorylation. The polysaccharide composition has potential development values in drug and health care products for treatment and prevention of the diseases. The polysaccharide composition may be developed and prepared into any formulation in pharmacy and is used for preventing and treating autoimmunity-related diseases in a single or composite medication form, including anti-aging, anti-tumor, anti-infection, antiviral and autoimmune diseases. The polysaccharide composition in the present application can be used for regulations of all activated nitric oxide synthaes and NO expressions and activated CD14/TRL4/P38 and TRL2/NF-kB path-related anti-tumor, antiviral, anti-infection and immunity related diseases.

The polysaccharide is a single chromatographic peak and has a molecular weight of 6880±50 Da and an optical rotation value of 158.4±0.5°. An infrared spectrum has a characteristic absorption peak at 847.6 cm-1. Hydrogen-proton characteristic chemical shifts in hydrogen spectra of the polysaccharide are $\delta 5.40$ brs, 3.95 t, J=7.2 Hz, 3.84 m and 3.61 m. Carbon signal characteristic chemical shifts in carbon spectra are $\delta 99.6$, $\delta 76.6$, $\delta 73.3$, $\delta 71.5$, $\delta 71.1$ and $\delta 60.4$.

A polysaccharide mass content in the polysaccharide composition is 92-98%; Agilent1200 liquid chromatography is adopted, a refractive index detector RID is used for analyzing, a chromatographic column is TSK-GEL G4000 PW×L, a mobile phase is ultrapure water, a flow velocity is 0.3-1 ml/min, a detector temperature is 30-40° C., a column temperature is 30-50° C., chromatographic analysis is a single peak, and retention time is 10-30 min. The polysaccharide is singly composed of α-D-glucopyranosyl, and the polysaccharide has an α-configuration and a connection manner of 1→4. One of a fluorescence labeled product, a carboxymethylation product, a hydroxymethylation product, a hydroxypropylation product, an ethylene glycol product, a propylene glycol product and a polyethylene glycol product is added into the polysaccharide composition.

A preparation method of the polysaccharide composition with the immunoregulation activity includes the following steps: step 1: performing water heating and extraction, and performing alcohol precipitation to prepare total polysaccharides; grinding *Polyporus umbellatus* Fries, adding 3 L of deionized water into 300 g of the ground *Polyporus umbellatus* Fries, soaking at room temperature for 1 hour, and heating at 100° C. and performing reflux extraction twice, extracting for 1 h each time, filtering, merging filtrates, concentrating to 600 ml, centrifuging at 3000 rpm for 10 min, regulating an ethanol ratio in a supernatant to be greater than 80%, standing overnight at 4° C., filtering the supernatant, precipitating and performing freeze-drying to obtain a crude polysaccharide, adding purified water into the crude polysaccharide to prepare a solution of 30 mg·mL$^{-1}$; step 2: removing crude polysaccharide protein; preparing sugar liquor, chloroform and n-butyl alcohol according to a ratio of 25:4:1, pouring into a separating funnel, fully shaking for 3 min, standing, layering, removing an organic layer and precipitates, repeatedly removing the protein until a white precipitate is not produced, collecting the supernatant, concentrating to an appropriate volume by using a rotary evaporator, transferring, and performing freeze-drying to obtain a crude polysaccharide without the protein; step 3: performing depigmentation by DEAE-52 cellulose; respectively adding a small amount of water into the crude polysaccharides without proteins and dissolving, discoloring using a pretreated DEAE-52 cellulose column of 35×3 cm, eluting with 1 mL/min of ultrapure water and 0.1-0.5% of sodium chloride solution, eluting until any sugar is not detected in effluent by using a phenol-dense sulfuric acid method, collecting eluant on a peak section, concentrating by using the rotary evaporator, performing freeze-drying, and desalting to obtain a white loose powdered pure polysaccharide; and step 4: refining by a Sephadex G-100 gel column; dissolving an appropriate amount of the pure polysaccharide into distilled water, adding the Sephadex G-100 gel column, eluting with pure water and 0.1-0.5% of sodium chloride solution, controlling flow velocity to 1 ml/min, collecting every 10 mL of the eluant into a tube, and tracking and monitoring by the phenol-dense sulfuric acid method; taking numbers of detection tubes as a horizontal coordinate and taking optical density as a vertical coordinate to draw a polysaccharide elution curve, collecting the eluant on the peak section, performing freeze-drying, and desalting to obtain the homogeneous polysaccharide.

A pretreatment method of the DEAE-52 cellulose column in the step 3 includes the following steps: step 11: soaking the cellulose of the dried powder in distilled water for 2-5 hours, removing impurities and draining; step 22: soaking with a 0.5 mol/L of HCL solution for 1-3 hours, washing with deionized water, regulating a pH to be neutral, and draining; and step 33: soaking the drained cellulose in a 0.5 mol/L of NaOH solution for 1-3 hours, washing with the deionized water, regulating the pH to be neutral, and draining.

By detecting the *Polyporus umbellatus* Fries polysaccharide composition prepared by the above method, the polysaccharide content is 96.73%. As shown in FIG. 1, Agilent1200 liquid chromatography is adopted, the refractive index detector RID is used for analyzing, the chromatographic column is TSK-GEL G4000 PW×L 10 mm, 7.8 mm I.D.×30 cm, the mobile phase is ultrapure water, the flow velocity is 0.5 ml/min, the detector temperature is 35° C., the column temperature is 40° C., chromatographic analysis is the single peak, and retention time is about 20 min.

Figure 2:
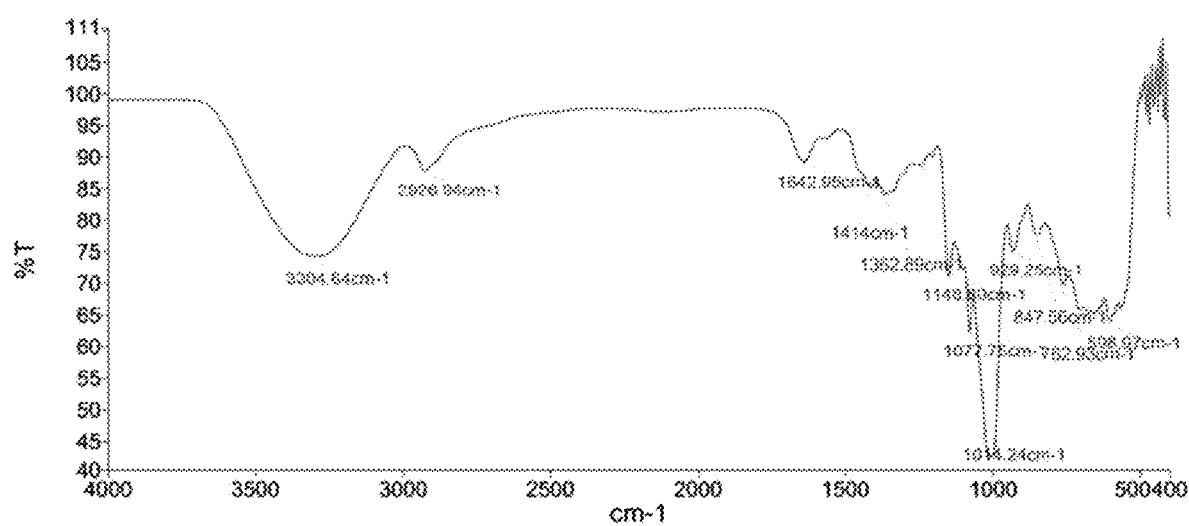
FIG. 2 is an infrared spectrogram of a *Polyporus umbellatus* Fries polysaccharide PPS.

Molecular-weight determination and structural identification of the *Polyporus umbellatus* Fries polysaccharide are as follows:

The molecular weight and monosaccharide composition of the separated and prepared *Polyporus umbellatus* Fries polysaccharide are determined by an entrusted third-party detection institution. As shown in FIG. 2, a weight-average molecular weight of the *Polyporus umbellatus* Fries polysaccharide is determined to be about 6.88 kDa by adopting HPGPC gel permeation chromatography. Results of the trifluoroacetic acid hydrolysis, acetic anhydride acetylation and GC-MS analysis of PPS show that, the *Polyporus umbellatus* Fries polysaccharide is singly composed of D-glucose. UV spectral analysis shows that end absorption at 190 nm is typical absorption of the polysaccharide, while if any absorption peak does not exist at 260 nm and 280 nm, it indicates that the PPS does not contain any nucleic acid or protein. IR spectroscopy shows typical polysaccharide characteristic absorption peaks (3304.6, 2926.9, 1642.9, 1362.9, 1148.8, 1077.8, 1014.2, 847.6 cm$^{-1}$). If any NH absorption peak is not shown in the IR spectroscopy, it indicates that the polysaccharide does not contain any amino or binding protein. An infrared spectrum of the PPS is basically consistent with an infrared spectrogram shown in FIG. 2.

Figure 3:
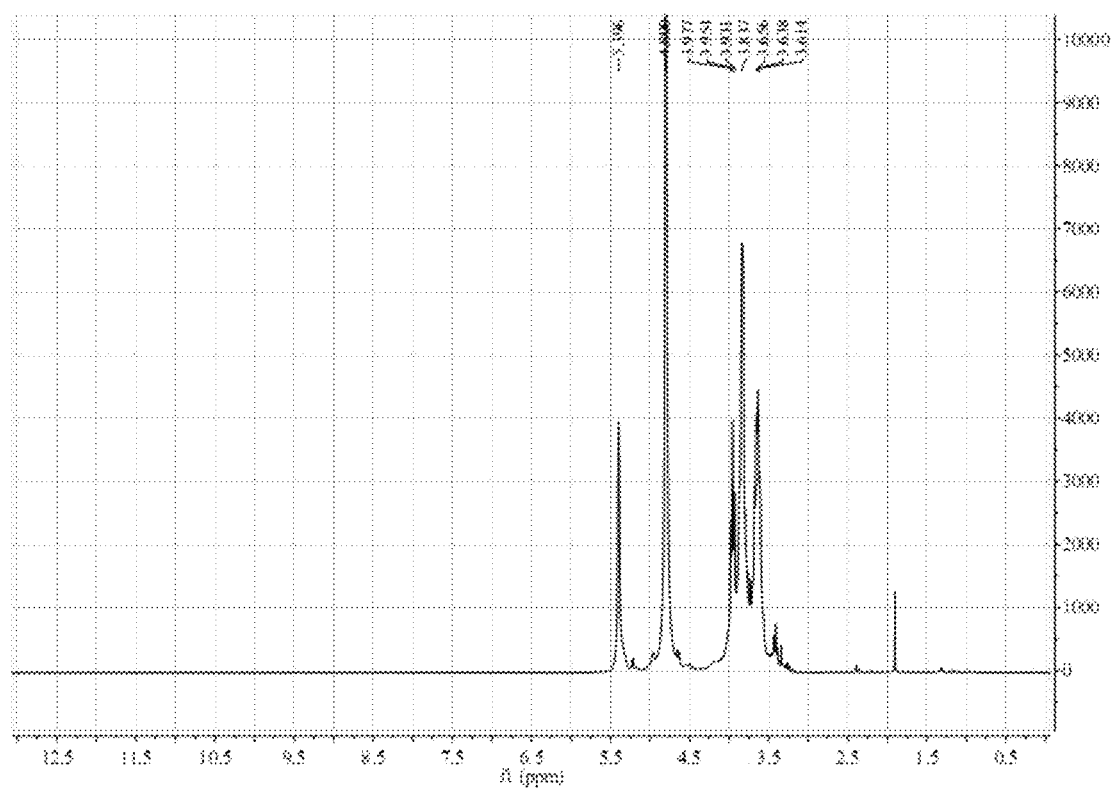
FIG. 3 is a spectrogram of a *Polyporus umbellatus* Fries polysaccharide PPS 1H-NMR (400 MHz, D2O)
Figure 4:
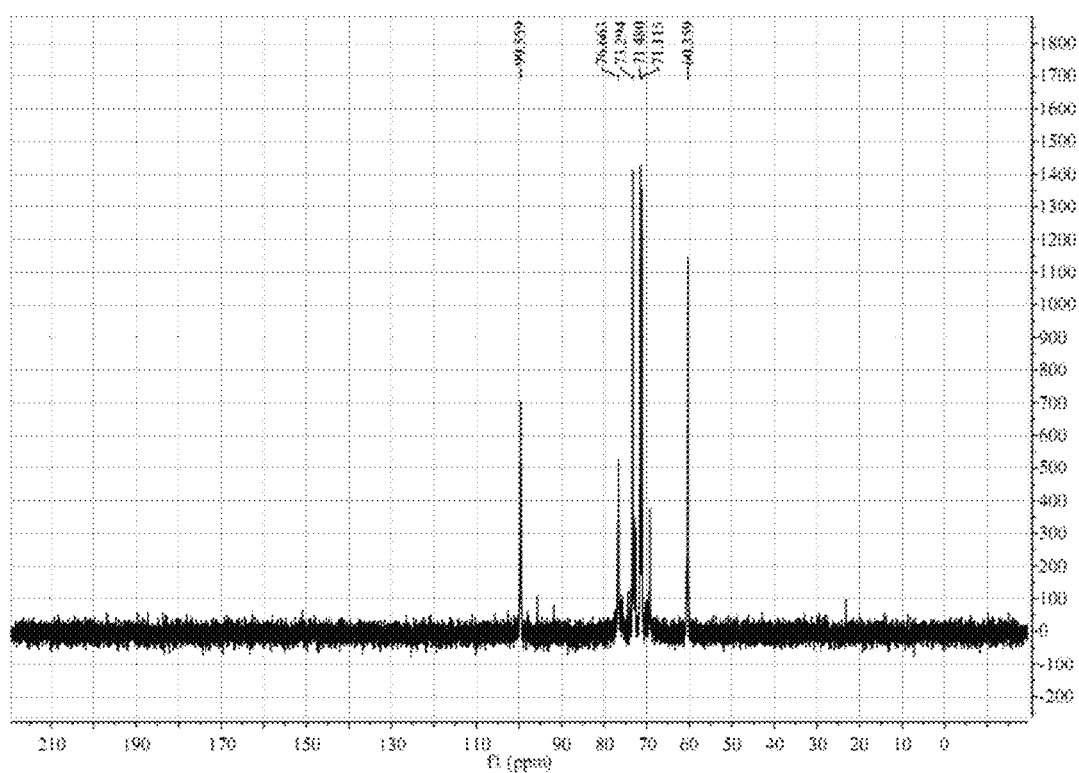
FIG. 4 is a spectrogram of a *Polyporus umbellatus* Fries polysaccharide PPS 13C-NMR (100 MHz, D2O)

Attribution of 1H-NMR (400 MHz, D2O): δ 5.40 ppm is a D-galactopyranose terminal hydrogen proton signal. A chemical shift value is greater than 5.0, and a broad single peak indicates that a connection manner of glucoside bonds is an α configuration; and a characteristic absorption peak exists at 847.6 cm$^{-1}$ in the infrared (IR) spectrum and a determined optical rotation value is a great specific rotation positive number (α25 D=+158.4±0.5 (c=2.5, H$_2$O)). All of the above may be further confirmed. Other hydrogen chemical shift intervals on the polysaccharide are in a range of 3.61-3.98 and are other proton signals on saccharide ring carbon, and the chemical shift values are all less than 4.0, which indicates that the polysaccharide does not have any other sugar residue anomeric hydrogen signal. Six main carbon signals are shown in a 13C-NMR (100 MHz, D2O) spectrum, and chemical position values of the carbon signals are respectively 99.6, 76.6, 73.3, 71.5, 71.1 and 60.4. In combination with a DEPT 135 spectrum, only δ 60.4 is a methylene functional group, and others are all methyne functional groups. It is hinted that, the monosaccharide composition of the polysaccharide is glucopyranose, and the methylene at the position 6 is not substituted. Through further combination of HSQC, HMBC and 1H-1H-COSY correlation-spectra analysis, carbon and hydrogen signals in the monosaccharide unit of the main composition of the PPS are subjected to complete attribution, wherein δ 99.6 is attributable to an anomeric carbon signal of glucose residues, δ 71.5, 71.1 and 73.3 are respectively glucose-unsubstituted C-2, 3, 5 carbon signals, δ 76.6 is a substituted C-4 resonance signal, δ 60.4 is an unsubstituted C-6 carbon signal, and the monosaccharide composition only contains α-D-glucopyranosyl, which is consistent with the above GC-MS and IR analysis result. The movement of chemical positions C-1(δ 99.6) and C-4(δ 76.6) to a low field shows that, hydroxyls at 1 and 4 positions of the monosaccharide are substituted, a connection manner between the monosaccharides is α-1→4 connection, which may be further confirmed by distant correlation of H-1(δ 5.40) and C-4(δ 76.6) as well as H-4(δ 3.61) and C-1(δ 99.6) in the HMBC spectrum. Other carbon signals with the chemical shift values of 99.7, 76.8, 72.8, 72.6, 71.6 and 69.3 may also be detected in the carbon spectrum, wherein the δ 69.3 is a substituted C-6 signal which indicates that a branched chain appears at a position O-6, while the δ 99.7, 76.8, 72.8, 72.6 and 71.6 are branched 1,4,6-α-D-glucopyranosyl C1-5 carbon signals. However, these signals have low intensity, which indicates that the position O-6 of the PPS has few branches. The above analysis shows that, the *Polyporus umbellatus* Fries polysaccharide PPS has a main connection manner of 1,4-, and partial branched chains or terminal glycosylated branched chains appear at the position O-6. Main signal values in the 1H-NMR and 13C-NMR spectrums of the PPS are basically consistent with signals in hydrogen and carbon spectra shown in FIG. 3 and FIG. 4.

Multiple experiments are made on immunomodulatory effects of the PPS by the present applicant. Specific experiments are as follows:

preparing reagents and materials:

cells: a murine macrophage cell line RAW264.7, cell line T24 ATCC of human bladder transitional cell carcinoma, preserved and provided by an inventor;

a high-glucose DMEM medium is purchased from Hyclone Company (batch number: SH3024.01B); Australian fetal calf serum, FBS (Hyclone, USA, batch number: SH30406.02E) double-antibody (GIBCO, USA); a PBS buffer solution (Hyclone, USA, batch number: SH30028.01B); IFN-γ interferon (Peprotech, USA); Trizol (Invitrogen, USA); a reverse transcription kit Revert Aid First Strand cDNA Synthesis Kit (Thermo, USA); and fluorescent quantitative PCR dye SYBR Green kit (Roche, USA);

cell culture performing conventional culture on the murine macrophage cell line RAW264.7 in DMEM containing 100 ml/L of fetal calf serum and 1% of double-antibody, placing at 37° C., and culturing in a 5% of $CO_2$ incubator;

preparation of tumor cell culture supernatant T24 culturing the cells of the human bladder transitional cell carcinoma cell line T24 in a DMED medium containing 10% of fetal calf serum and 100 U/ml of penicillin streptomycin, and placing in a 5% of $CO_2$ incubator at 37° C.; culturing T24 cells in logarithmic growth in a culture dish at cell population of $3.5×10^7$ cells/well, adding 18 ml of culture solution, culturing for 48 h until the cells grow to confluence of 90%, and collecting a culture supernatant for later use; and filtering the collected culture supernatant by a filter of 0.22 μm, and cryopreserving the filtered culture supernatant in a refrigerator at −80° C. and preserving for later use;

co-culture of T24 cells and RAW264.7 cells culturing the cells in the murine macrophage cell line RAW264.7 in the DMED medium containing 10% of fetal calf serum and 100 U/ml of penicillin streptomycin, and placing in a 5% of $CO_2$ incubator at 37° C.; and performing co-culture on the RAW264.7 cells in a logarithmic growth period and the T24 supernatant, wherein a culture solution of 40% is the T24 tumor cell culture supernatant.

Figure 5:
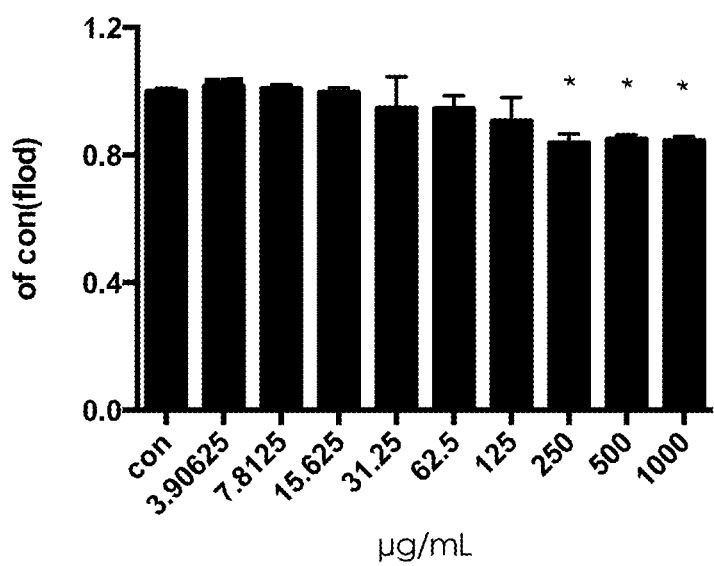
FIG. 5 is a schematic diagram of an influence of a *Polyporus umbellatus* Fries polysaccharide PPS on a RAW264.7 cell survival rate.

An influence of the *Polyporus umbellatus* Fries polysaccharide PPS on a survival rate of the RAW264.7 cells is tested as follows:

inoculating RAW264.7 cell suspension into a 96-well plate at a density of 104 cells/well, culturing for 24 h, and then removing old liquid; respectively adding culture media of the PPS with a series of concentrations of 3.09625, 7.8125, 15.625, 31.25, 62.5, 125, 250, 500 and 1000 μg/mL; culturing for 24 h; adding 20 μL, of 50 g·L-1 MTT solution into each well, continuously incubating for 4 h, removing the supernatant, adding 200 μL of DMSO into each well, dissolving at room temperature, shaking for 10 min, and then determining an optical density (OD) value at a wavelength of 490 nm in an ELISA analyzer. Each drug concentration is repeated in every 4 wells. A relative survival rate of the cells is calculated, and a formula is as follows: the relative survival rate of the cells=OD490(medication)/OD490(control), wherein the OD490(medication) and the OD490(control) are respectively adsorption values of a cell sample in a medication group and a cell sample in a control group at 490 nm in an MTT experiment. An influence of the PPS on the survival rate of the RAW264.7 macrophages is shown in FIG. 5. It can be seen that, the cell survival rate does not have any statistical significance compared with the control group when the drug concentration is in a range of 3.9-125 mg/mL, so gradient concentrations selected by subsequent PPS experiments are 1, 10 and 100 mg/mL.

Figure 6A:
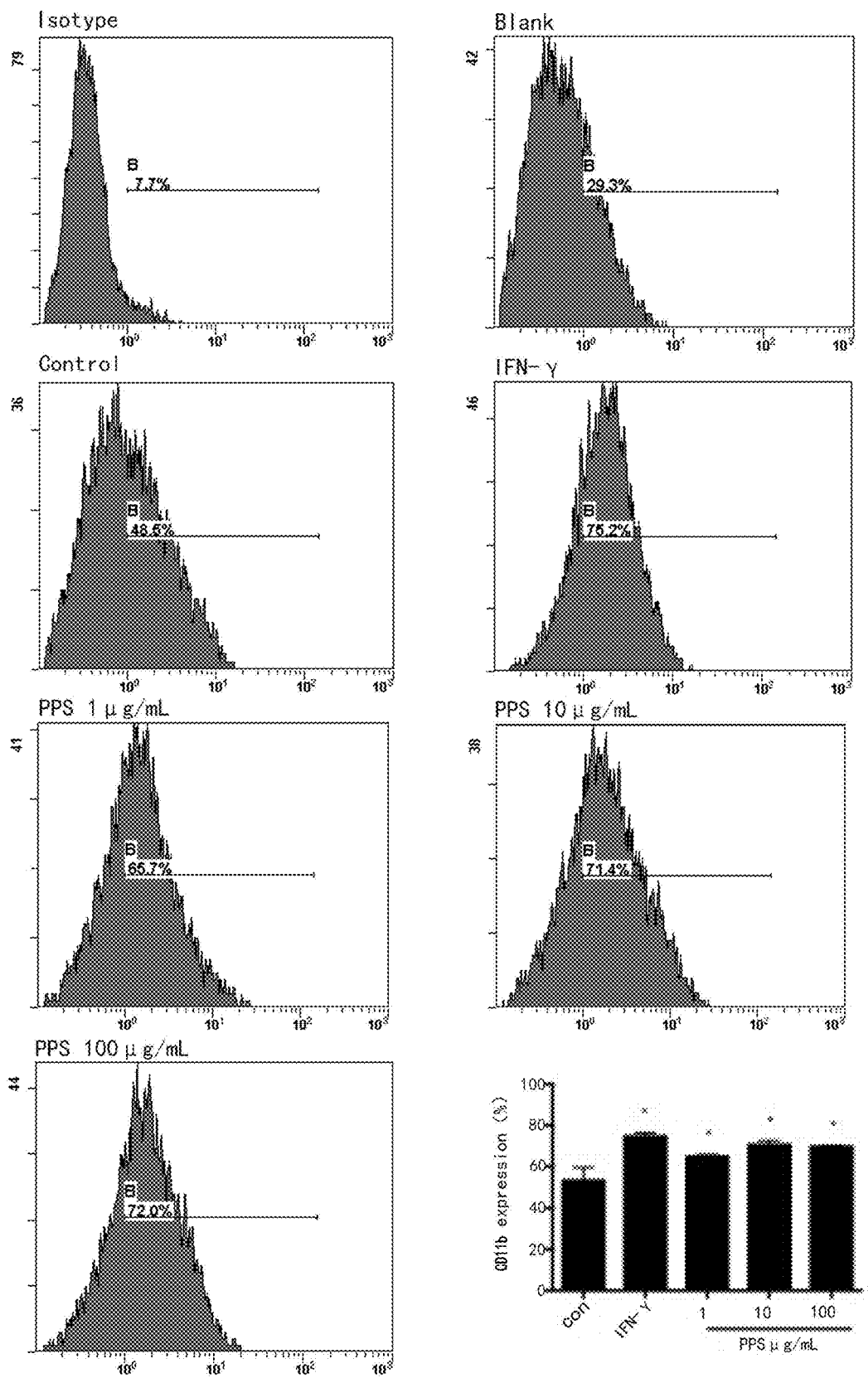
FIG. 6a is a schematic diagram of an expression influence of a *Polyporus umbellatus* Fries polysaccharide PPS on a RAW264.7 cell membrane surface molecule CD11b.
Figure 6B:
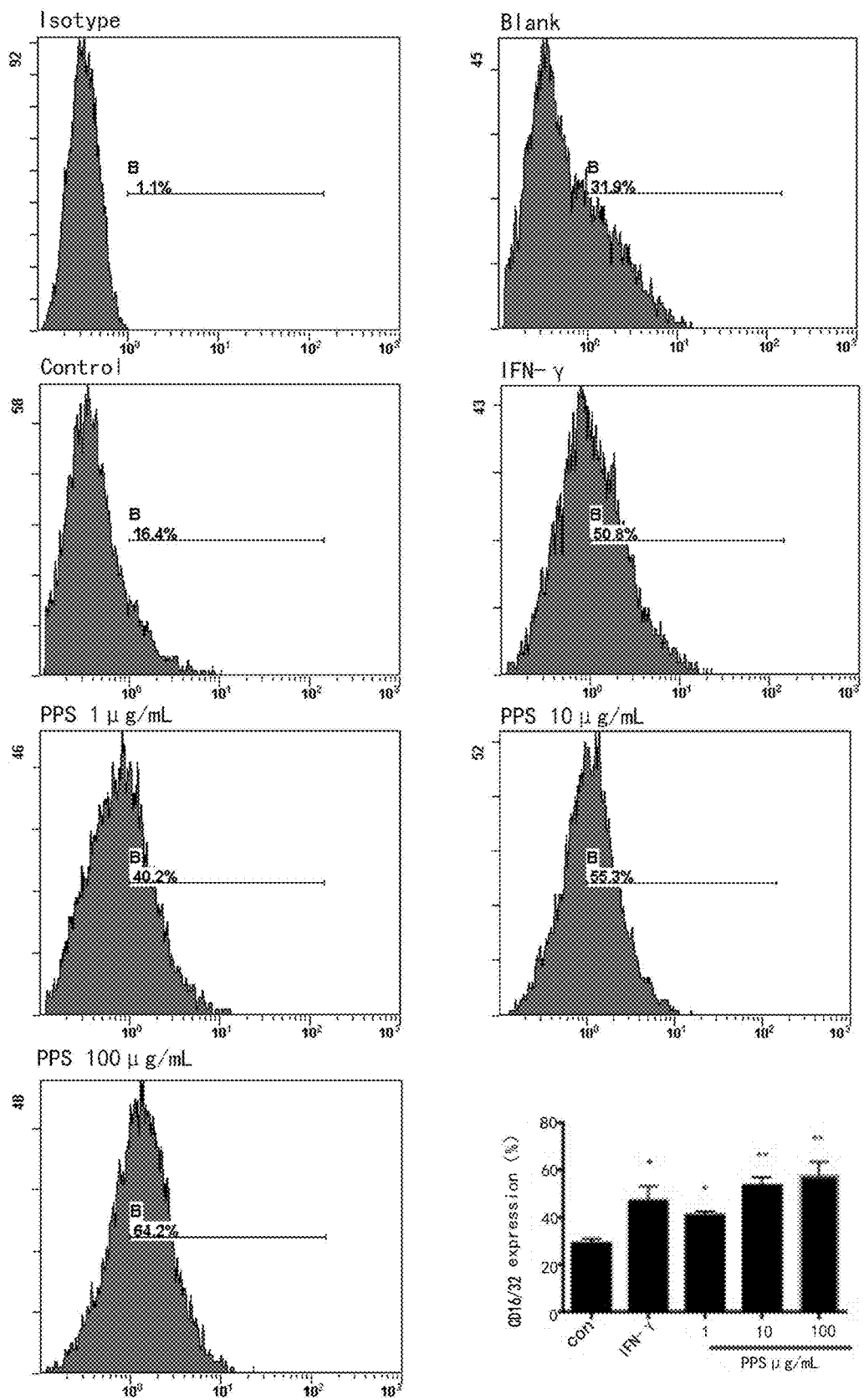
FIG. 6b is a schematic diagram of an expression influence of a *Polyporus umbellatus* Fries polysaccharide PPS on a RAW264.7 cell membrane surface molecule CD16/32.
Figure 6C:
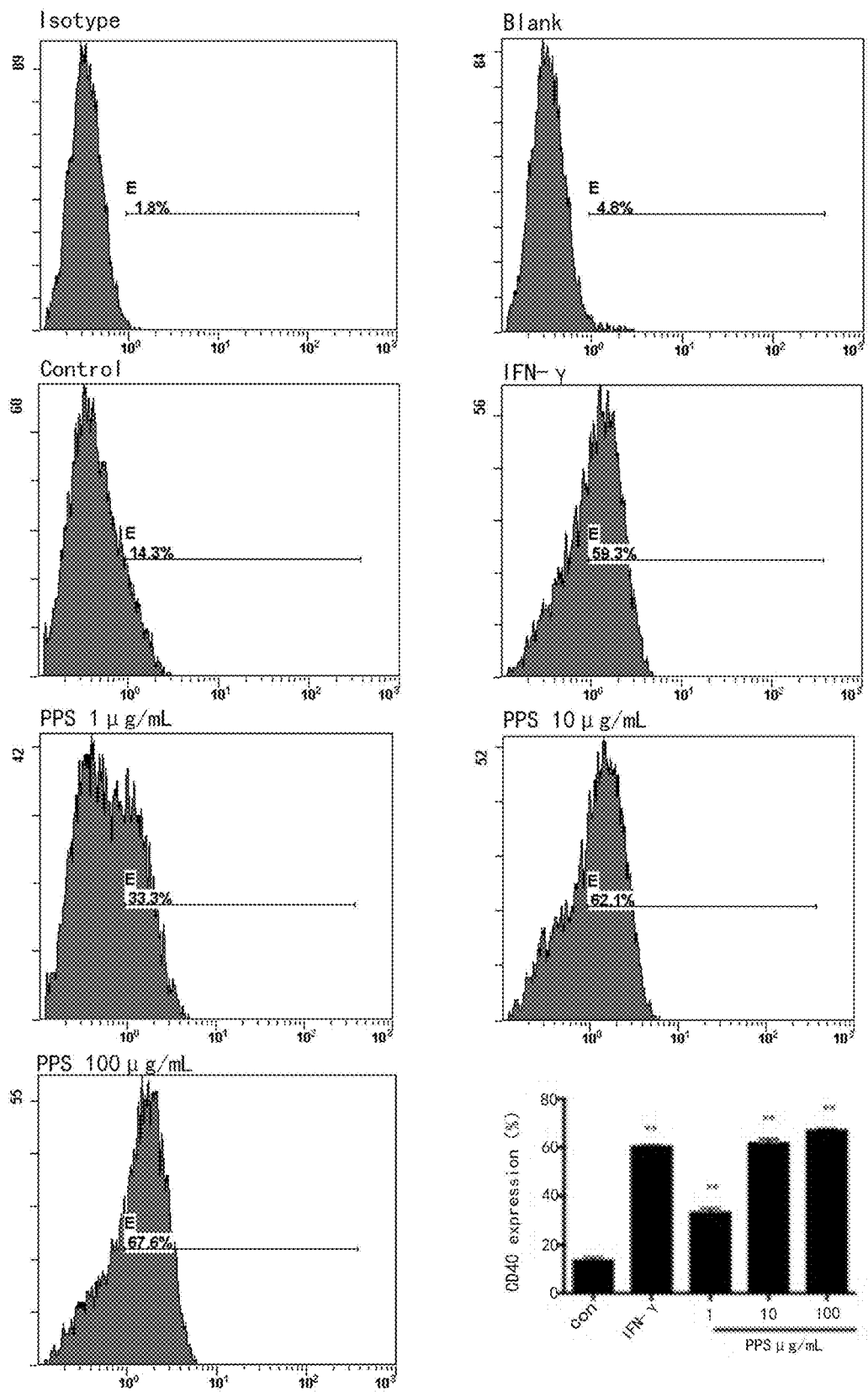
FIG. 6c is a schematic diagram of an expression influence of a *Polyporus umbellatus* Fries polysaccharide PPS on a RAW264.7 cell membrane surface molecule CD40.

An influence of the PPS on a RAW264.7 macrophage membrane surface molecule in a co-culture system of T24 and RAW264.7 cell is tested as follows:

performing conventional culture on the murine macrophage cell line RAW264.7 in a DMEM culture solution containing 100 ml/L of fetal calf serum; selecting cells in a logarithmic growth period, performing digestion passage, counting and adjusting cell density, inoculating the cells into a 12-well cell culture plate according to $2.5×10^5$ cells per well, and adding 1 ml of DMEM medium into each well; culturing for 24 h until the cells are completely adherent; removing 0.5 mL of the medium, and adding 0.5 mL of T24 supernatant; after 3 h, respectively adding an IFN-γ solution with a final concentration of 100 ng/mL and 1, 10 and 100 μg/mL of the PPS to act for 24 h; digesting and collecting the cells in a flow tube, adding 2 mL of PBS for washing for 3 times, and centrifuging by 1000 revolutions to remove the supernatant; sequentially adding corresponding flow antibodies of CD16/32-FITC, CD40-PE and CD11b-APC by 5 μL respectively, and taking a corresponding isotype antibody as negative control; keeping in dark at 4° C., incubating for 30 min, washing with PBS, and centrifuging to wash a free flow antibody; and resuspending the cells with 500 μL of PBS and detecting a positive expression rate of an associated membrane surface molecule by a flow cytometer. Results are shown in FIG. 6A as follows: the PPS can increase the expression quantity of CD11b of the macrophage, and a statistical significance (P<0.05) is achieved compared with the control group; as shown in FIG. 6B, the macrophages may be stimulated by the 1, 10 and 100 μg/mL of the PPS, the expression of CD40 is increased, and an obvious statistical significance (P<0.01) is achieved; as shown in FIG. 6C, the 1, 10 and 100 μg/mL of the PPS can increase the expressions of macrophages CD16/32, and a statistical significance is achieved. Compared with the control group, PPS groups with concentrations of 10 and 100 μg/mL have an obvious statistical significance (P<0.01). The CD11b, CD16/32 and CD40 are all membrane markers for polarizing the macrophages into Ml, which indicates that the PPS may activate the macrophages at a lower dosage of 1 μg/mL.

Figure 7A:
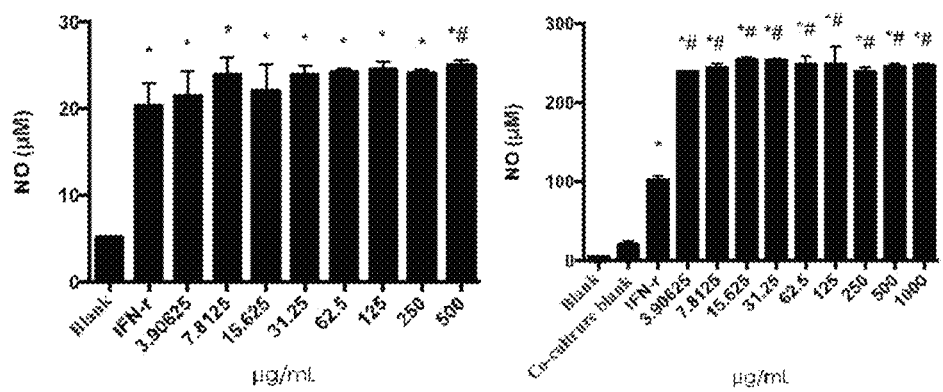
FIG. 7A is a schematic diagram of an influence of a *Polyporus umbellatus* Fries polysaccharide PPS on an NO secretion amount in a co-culture system of human transitional bladder cancer T24 cells and RAW264.7 macrophage.
Figure 7B:
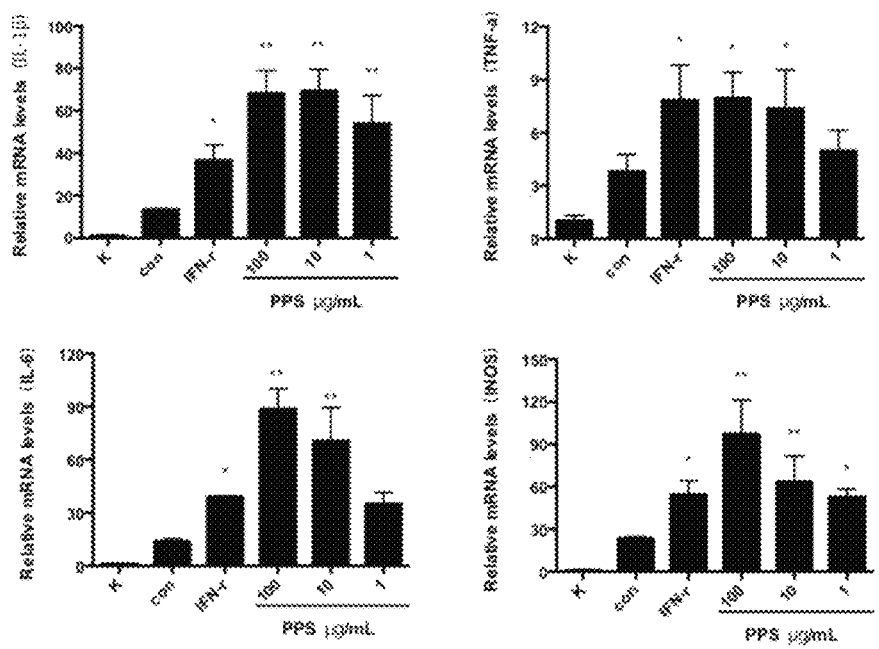
FIG. 7B is a schematic diagram of an influence of a *Polyporus umbellatus* Fries polysaccharide PPS on an inflammatory factor in a co-culture system of human transitional bladder cancer T24 cells and RAW264.7 macrophage.

Influences of the *Polyporus umbellatus* Fries polysaccharide PPS on NO actor secretion and the expression quantity of IL-1β, IL-6, TNF-α and iNOS mRNA in macrophages RAW264.7 are tested as follows:

taking macrophages RAW264.7 in a good growing status, performing digestion passage, counting and adjusting cell density, inoculating the cells into a 12-well cell culture plate, adding 1 ml of cell suspension; adding $2.5 \times 10^5$ RAW264.7 cells into each well, culturing in a 5% of $CO_2$ incubator at 37° C. for 24 h, then adding an IFN-γ solution with a final concentration of 100 ng/mL into a positive group, and respectively adding PPS with concentrations of 3.09625, 7.8125, 15.625, 31.25, 62.5, 125, 250, 500 and 1000 μg/mL into medication groups and culturing for 24 h; culturing the cells in a co-culture group for 24 h, then removing 40% of the supernatant, adding 40% of T24 supernatant, totally culturing for 3 hours, then adding the IFN-γ solution with the final concentration of 100 ng/mL into the positive group, and respectively adding the PPS with concentrations of 3.09625, 7.8125, 15.625, 31.25, 62.5, 125, 250, 500 and 1000 μg/mL into each of the medication groups and culturing for 24 h; and collecting the cell supernatant, and detecting the secretion quantity of the NO cell factor by a Griess method. Experimental results are shown in FIG. 7A. The results show that, the PPS stimulates to secrete more NO at 3.9 g/m compared with IFN-γ (100 ng/mL), and can obviously promote the macrophages to secrete the NO in a simulated bladder carcinoma tumor microenvironment (co-culture of macrophages and bladder carcinoma cells). Moreover, the NO secretion quantity at a lower dosage of 3.90625 μg/mL is higher than that of the IFN-γ (100 ng/mL) by more than 2 times in a positive control group;

inoculating $2.5 \times 10^5$ cells into the 12-well cell culture plate, culturing for 24 h, removing 40% of the supernatant, adding 40% of the T24 supernatant, culturing for 3 hours, then adding the IFN-γ solution with the final concentration of 100 ng/mL and the PPS of 1, 10, 100 μg/mL and culturing for 24 h; removing the cell supernatant, adding 600 μL of Trizol lysate into each well, and collecting the cells; and detecting the expression quantity of genes IL-1β, IL-6, TNF-α and INOS by an RT-PCR method. Experimental results are shown in FIG. 7B. The PPS can obviously increase the expression quantity of the genes IL-1β, IL-6, TNF-α and INOS in the macrophages in the simulated bladder carcinoma tumor microenvironment, which indicates that the PPS can activate the macrophages in the tumor microenvironment. Primer sequences are shown in Table 1 as follows:

TABLE 1

Primer sequences

| Gene | Sense strand (5'-3') | Antisense strand (5'-3') |
| --- | --- | --- |
| IL-6 | TACTCGGCAAACCTAGTGCG | GTGTCCCAACATTCATATTGTCAGT |
| INOS | CGGCAAACATGACTTCAGGC | GCACATCAAAGCGGCCATAG |
| TNF-a | GGGGATTATGGCTCAGGGTC | CGAGGCTCCAGTGAATTCGG |
| IL-1β | CCATGGAATCCGTGTCTTCCT | GTCTTGGCCGAGGACTAAGG |
| GAPDH | TTTGTCAAGCTCATTTCCTGGTATG | TGGGATAGGGCCTCTTGC |

Figure 8:
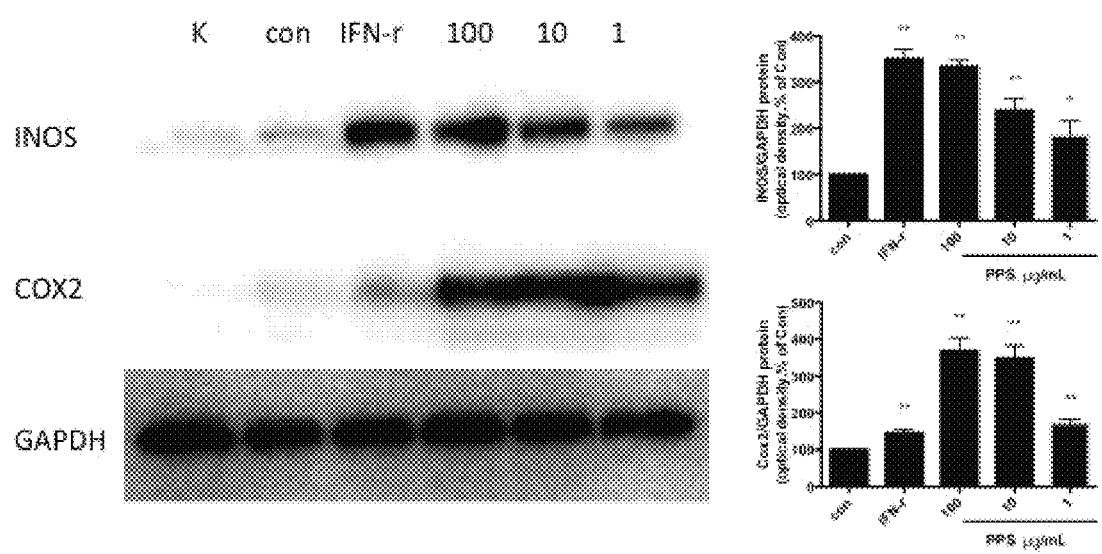
FIG. 8 is a schematic diagram of an influence of a *Polyporus umbellatus* Fries polysaccharide PPS on COX2 and INOS mRNA protein expressions in a co-culture system of T24 and RAW264.7 cells.
Figure 9A:
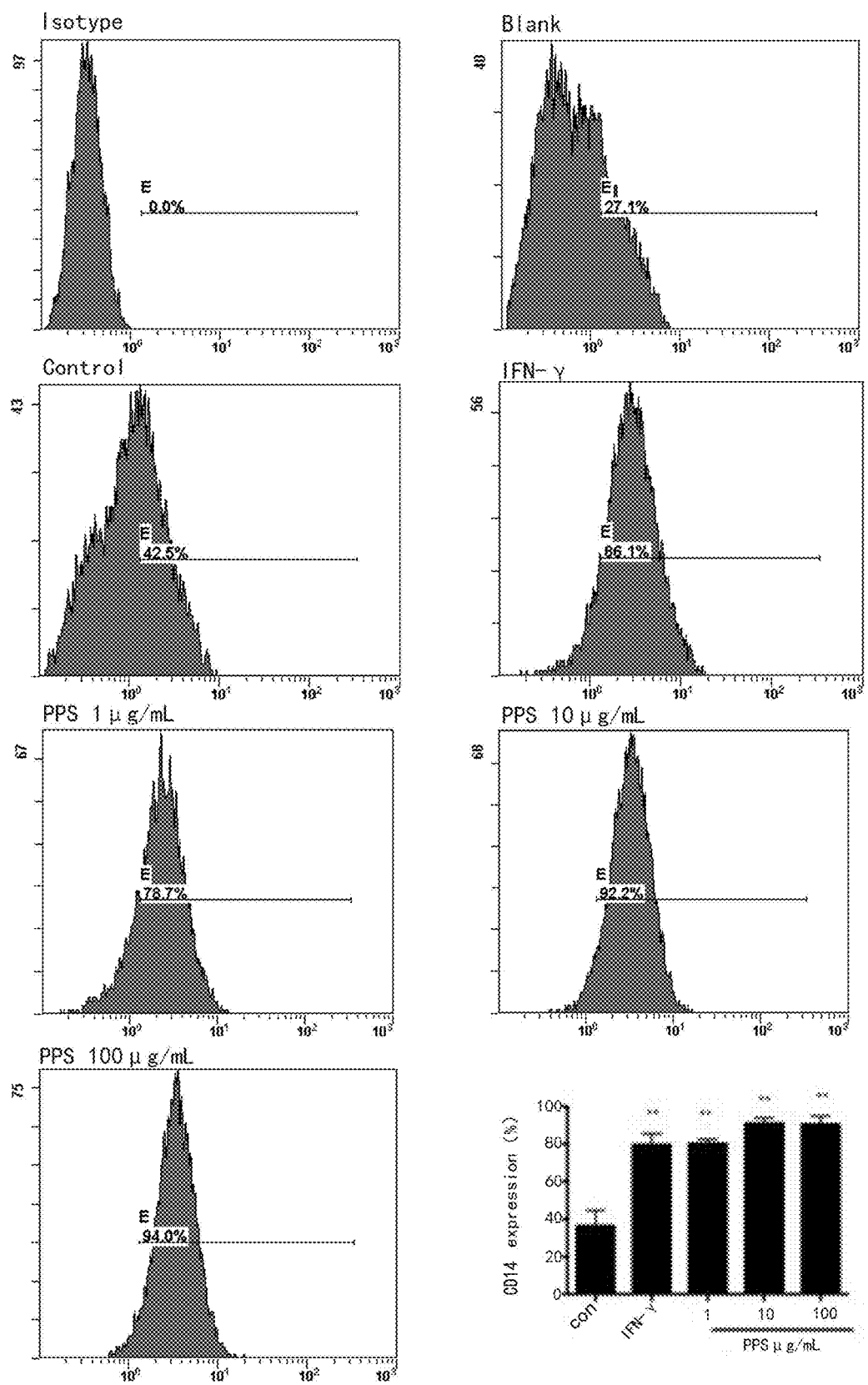
FIG. 9a is a schematic diagram of an action of a *Polyporus umbellatus* Fries polysaccharide PPS on CD14 protein tyrosine phosphorylation expression.
Figure 9B:
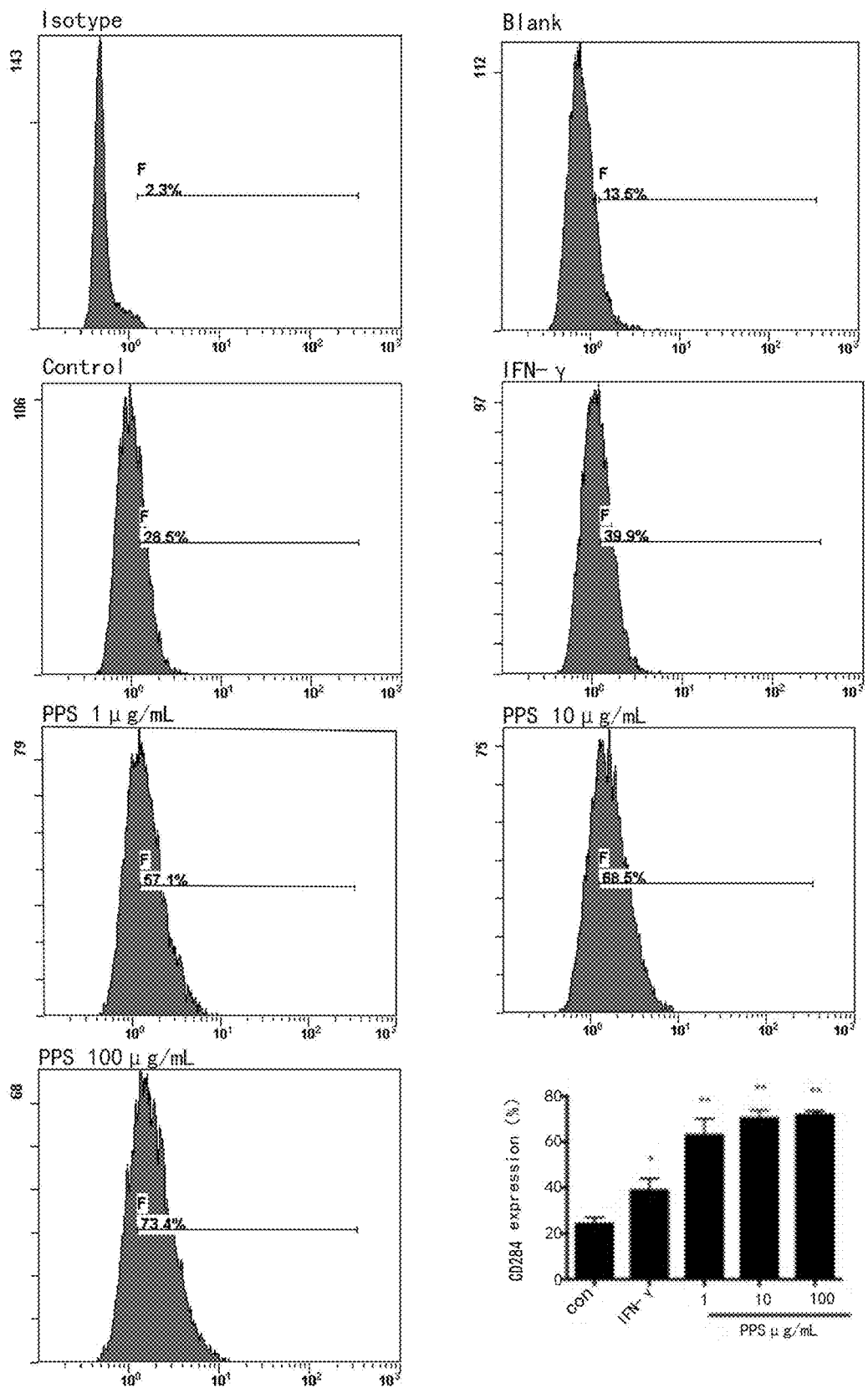
FIG. 9b is a schematic diagram of an action of a *Polyporus umbellatus* Fries polysaccharide PPS on CD284 protein tyrosine phosphorylation expression.
Figure 9C:
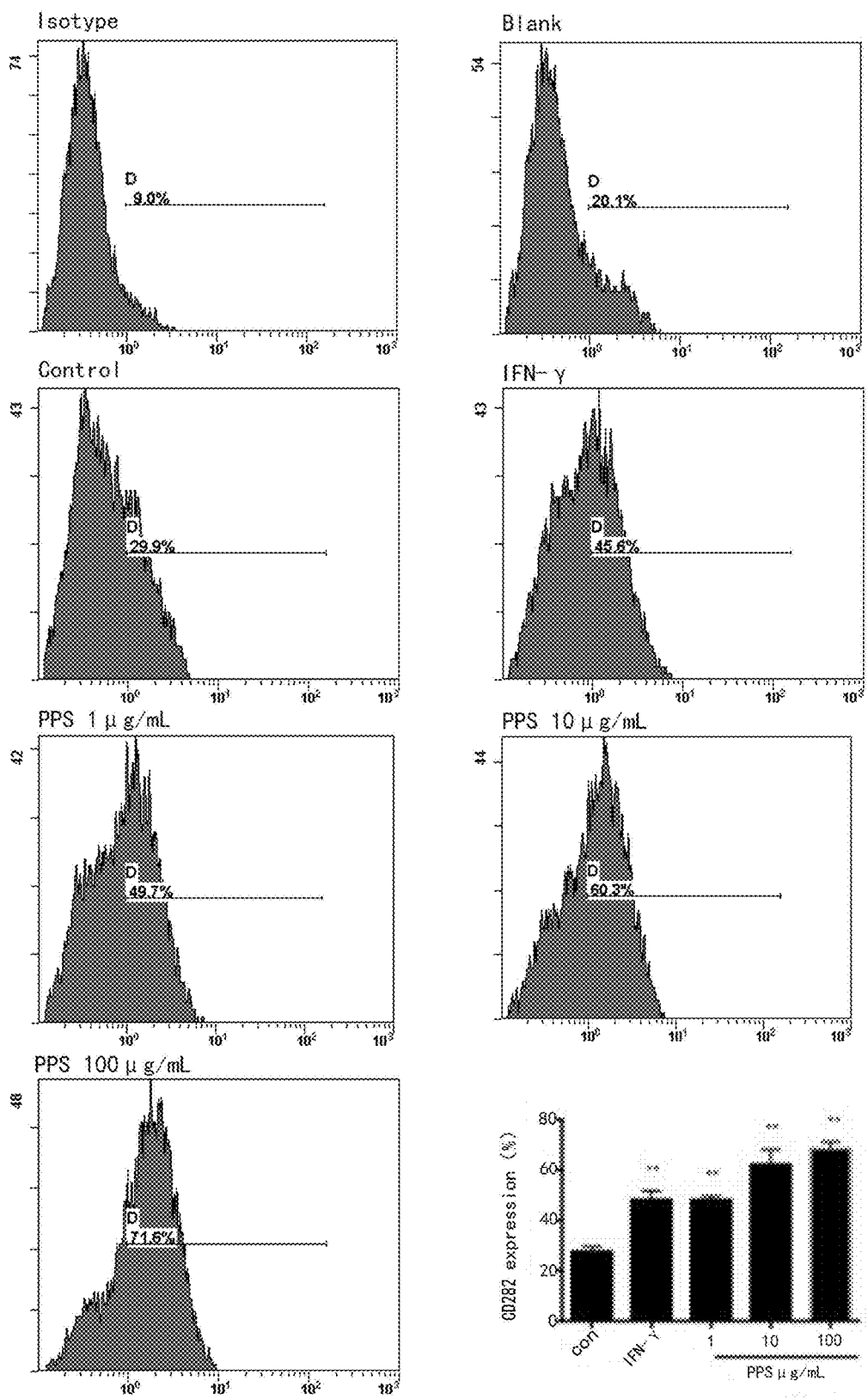
FIG. 9c is a schematic diagram of an action of a *Polyporus umbellatus* Fries polysaccharide PPS on CD282 protein tyrosine phosphorylation expression.
Figure 9D:
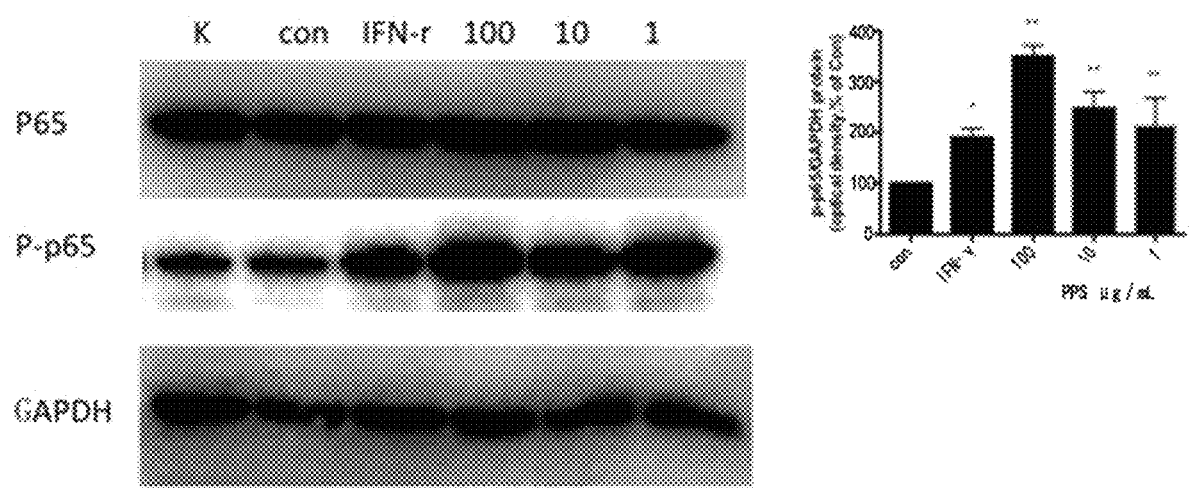
FIG. 9d is a schematic diagram of an action of a *Polyporus umbellatus* Fries polysaccharide PPS on P38 protein tyrosine phosphorylation expression.
Figure 9E:
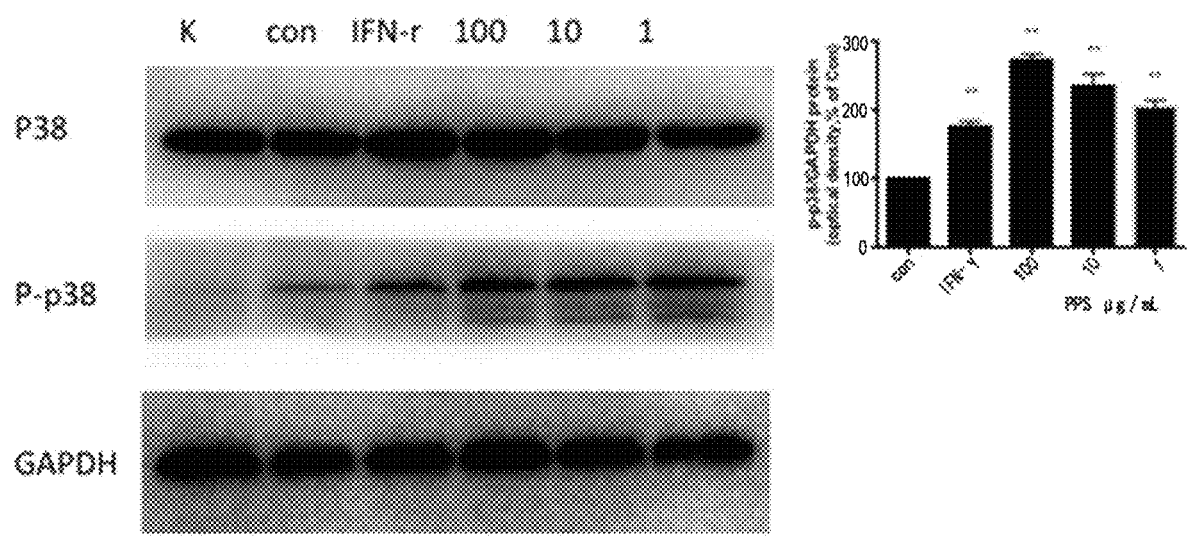
FIG. 9e is a schematic diagram of an action of a *Polyporus umbellatus* Fries polysaccharide PPS on P65 protein tyrosine phosphorylation expression.

Influences of the *Polyporus umbellatus* Fries polysaccharide PPS on protein expressions of COX2 and INOS in a co-culture system of T24 and RAW264.7 cells are tested as follows:

performing conventional culture on the macrophage cell line RAW264.7 in a DMEM culture solution containing 100 ml/L of fetal calf serum; selecting cells in a logarithmic growth period and inoculating in a 6-well cell culture plate; removing 0.8 mL of the medium within 24 h after complete adherence, adding 0.8 mL of a T24 supernatant, and totally culturing for 3 h; and adding the IFN-γ solution with the final concentration of 100 ng/mL and the PPS of 1, 10, 100 μg/mL to act for 24 h. It can be seen from Western-blot data analysis, compared with the control group, the PPS of 1, 10, 100 μg/mL respectively has an effect of obviously increasing INOS and COX2 protein tyrosine phosphorylation expressions (FIG. 8), which indicates that the PPS can activate the macrophages in the bladder carcinoma tumor microenvironment and increase the expression of the INOS and COX2 proteins, thereby achieving the immunomodulatory effects.

Study on mechanisms of the PPS that activates macrophage CD14/TRL4/P38MAPK and TRL2/NF-kB related paths:

performing conventional culture on the murine macrophage cell line RAW264.7 in a DMEM culture solution containing 100 ml/L of fetal calf serum; selecting cells in a logarithmic growth period, performing digestion passage, counting and adjusting cell density, inoculating the cells into a 6-well cell culture plate according to $1 \times 10^6$ cells/well; culturing for 24 h until the cells are completely adherent; removing 0.8 mL of the medium, adding 0.8 mL of T24 supernatant, and culturing for 3 h; respectively adding an IFN-γ solution with a final concentration of 100 ng/mL and 1, 10 and 100 μg/mL of the PPS to act for 24 h; removing the supernatant, adding a pre-cooled PBS buffer solution to wash twice, then adding an appropriate amount of RIPA lysate (adding a phosphatase inhibitor and a protease inhibitor), scraping the cells on ice, centrifuging by 15000×g for 15 min, and taking the supernatant, i.e., a total cell protein solution; adding loading buffer and ultrapure water at 100° C. for 10 min. It can be seen from Western-blot data analysis, compared with the control group, the PPS of the 1, 10, 100 μg/mL has effects of obviously activating expressions of receptors CD14, CD284(TLR4) and CD282(TLR2) and increasing P-P38 and P-P65 protein tyrosine phosphorylation expressions (FIG. 9), which indicates that the PPS that activates the macrophages in the bladder carcinoma tumor microenvironment may achieve the immunomodulatory effects by activating the CD14/TRL4/P38 MAPK and TRL2//NF-kB paths.

In conclusion, the *Polyporus umbellatus* Fries polysaccharide PPS has an important bioregulation activity. The CD11b, CD16/32 and CD40 are all membrane marker proteins for polarizing the macrophages into Ml. In the present experiment, after interfering with the macrophages, the *Polyporus umbellatus* Fries polysaccharide PPS can obviously increase expressions of membrane molecules, such as CD11b, CD16/32, CD40 and the like, in the macrophages RAW264.7, which indicates that the PPS can activate the macrophages in the tumor microenvironment. The NO extensively participates in multi-system physiological and pathological processes of a body that generates immune response and inflammatory response and can adjust immunologic functions of the macrophages, T lymphocytes, B lymphocytes, NK cells and the like. The NO produced by the activated macrophages is used as a specific effect factor and can kill or inhibit growth of multiple pathogenic microorganisms, and mainly kill pathogens in the cells. The present experimental study discovers that (the purified *Polyporus umbellatus* Fries polysaccharide) PPS can promote NO secretion of the macrophages, and at a lower dosage of 3.90625 μg/mL, the NO secretion is close to that of the IFN-γ (100 ng/mL). The NO secretion of the macrophages can be promoted in the bladder carcinoma tumor microenvironment, and the NO secretion at the lower dosage of 3.90625 μg/mL is higher than that of the IFN-γ (100 ng/mL) in a positive control group, which indicates that the PPS can increase non-specific immune response of the body at the lower dosage regardless of a co-culture environment or a non-co-culture environment, thereby enhancing the immunologic function of the body.

Signal paths p38 MAPK and NF-kB are two important immune inflammatory paths. Our experimental study discovers that, after actions of the PPS, the expressions of the CD14, TRL4 and pp38 proteins are increased in the bladder carcinoma tumor microenvironment, which indicates that the *Polyporus umbellatus* Fries polysaccharide PPS may activate the macrophages by activating a signal path axis of CD14/TRL4/P38. Meanwhile, the TRL2 and PP65 protein expressions of the macrophages after the actions of the PPS are increased in the tumor microenvironment, which indicates that TRL2/NF-kB may also be one of the paths for promoting activation of the macrophages by the PPS.

Interferon (IFN-γ) is an important cellular immune factor and achieves an anti-tumor effect by regulating immunity of the body. The IFN-γ can activate the macrophages, secrete the NO, enhance the capability produced by antigen presenting cell MHCII type molecules in the macrophages and enhance presenting capability to antigens. In addition, the IFN-γ can enhance the capability of killing the macrophages and NK cells, increase the expressions of cell surface antigens and receptors and inhibiting functions of B cells, thereby lowering a level of blocking antibodies on tumor cell surfaces. The present experimental study discovers that (the purified *Polyporus umbellatus* Fries polysaccharide) PPS can secrete the NO in a non-tumor microenvironment and the bladder carcinoma tumor microenvironment, which indicates that the PPS has effects of activating the macrophages and regulating the immunologic functions. The IFN-γ is also a broad-spectrum antiviral drug. Effects of the PPS in the non-tumor microenvironment and the bladder carcinoma tumor microenvironment are similar to those of the IFN-γ. The secreted NO can inhibit replication of viruses in vivo. Meanwhile, the IFN-γ is an anti-tumor drugs and can secrete TNF-α to directly kill tumor cells and secrete IL-6 and IL-1β to regulate an inflammatory microenvironment, thereby enhancing immunosurveillance on the tumor cells.

Safety is a key point of drug evaluation. Biomacromolecule antigens are clinically used for treating tumors and other diseases, but may cause many severe side effects, such as marrow suppression, decrease of peripheral blood leucocytes and blood platelets, influenza-like syndromes, renal damage and the like. At present, any adverse reaction of *Polyporus umbellatus* Fries in a clinical application is not reported, while the PPS is a macromolecular component extracted from a relatively safe traditional Chinese medicine *Polyporus umbellatus* Fries in clinical medication and is safer than the IFN-γ. Therefore, it is indicated that, the PPS has potential development values in drug and health care products for treatment and prevention of the diseases.

By taking the above ideal embodiments of the present invention as revelation, related staff may completely make diversified changes and modifications on premise of not deviating from a scope of a technical idea of the present invention by virtue of the above description. A technical scope of the present invention is not limited to contents in the description, and must be determined according to a scope of claims.

What is claimed is:

1. A preparation method of a polysaccharide composition comprising the following steps:

step 1: performing water heating and extraction, and performing alcohol precipitation to prepare total polysaccharides comprising: grinding *Polyporus umbellatus* Fries, adding 3 L of deionized water into 300 g of the ground *Polyporus umbellatus* Fries, soaking at room temperature for 1 hour, and heating at 100° C. and performing reflux extraction twice, extracting for 1 h each time, filtering, merging filtrates, concentrating to 600 ml, centrifuging at 3000 rpm for 10 min, regulating an ethanol ratio in a supernatant to be greater than 80%, standing overnight at 4° C., filtering the supernatant, precipitating and performing freeze-drying to obtain a crude polysaccharide, adding purified water into the crude polysaccharide to prepare a crude polysaccharide solution at 25-35 mg·mL$^{-1}$;

step 2: removing crude polysaccharide protein comprising: preparing the crude polysaccharide solution, chloroform and n-butyl alcohol according to a ratio of 25:4:1, pouring the above components into a separating funnel, fully shaking for 3 min, standing, layering, removing an organic layer and precipitates, repeatedly removing the protein until a white precipitate is not produced, collecting the supernatant, concentrating to an appropriate volume by using a rotary evaporator, transferring, and performing freeze-drying to obtain a protein-free crude polysaccharide;

step 3: performing depigmentation by DEAE-52 cellulose comprising: adding a small amount of deionized water into the protein-free crude polysaccharide, prepared in step 2, and dissolving, discoloring using a pretreated DEAE-52 cellulose column of 35×3 cm, eluting with 1 mL/min of ultrapure water and 0.1-0.5% of sodium chloride solution, eluting until any sugar is not detected in effluent by using a phenol-dense sulfuric acid method, collecting the eluant on a peak section, concentrating by using the rotary evaporator, performing freeze-drying, and desalting to obtain a white, loose powdered, pure polysaccharide; and step 4: refining by a Sephadex G-100 gel column comprising: dissolving the pure polysaccharide, prepared in step 3, into distilled water, adding the Sephadex G-100 gel column, eluting with pure water and 0.1-0.5% of sodium chloride solution, controlling flow velocity to 1 ml/min, collecting every 10 mL of the eluant into a tube, and tracking and monitoring by the phenol-dense sulfuric acid method; taking numbers of detection tubes as a horizontal coordinate and taking optical density as a vertical coordinate to draw a polysaccharide elution curve, collecting the eluant on the peak section, performing freeze-drying, and desalting to obtain the polysaccharide composition.

2. The preparation method according to claim 1, wherein a pretreatment method of the DEAE-52 cellulose column in the step 3 comprises the following steps:

step 1: soaking the cellulose of dried powder in distilled water for 2-5 h, removing impurities and then draining;

step 2: soaking the drained cellulose without the impurities in step 1 by using a 0.5 mol/L of HCL solution for 1-3 h, washing with deionized water, regulating a pH to be neutral, and draining; and step 3: soaking the drained cellulose in step 2 in a 0.5 mol/L of NaOH solution for 1-3 h, washing with the deionized water, regulating the pH to be neutral, and draining.

3. A polysaccharide composition with immunoregulation activity, for activation of toll-like receptor 2 (TLR2), produced by the method of claim 1, comprising a polysaccharide being a single chromatographic peak, wherein the homogeneous polysaccharide has a molecular weight of 6880±50 Da and an optical rotation value of 158.4±0.5°;

an infrared spectrum has a characteristic absorption peak at 847.6 cm$^{-1}$;

hydrogen-proton NMR characteristic chemical shifts of the polysaccharide are δ5.40 (brs), 3.95 (t, J=7.2 Hz), 3.84 (m) and 3.61 (m); and carbon NMR signal characteristic chemical shifts of the polysaccharide are δ99.6, δ76.6, δ73.3, δ71.5, δ71.1 and δ60.4.

4. The polysaccharide composition according to claim 3, wherein mass content of the polysaccharide, in the polysaccharide composition, is 92-98%;

Agilent 1200 liquid chromatography is adopted, a refractive index detector RID is used for analyzing, a chromatographic column is TSK-GEL G4000 PW×L, a mobile phase is ultrapure water, a flow velocity is 0.3-1 ml/min, a detector temperature is 30-40° C., a column temperature is 30-50° C., chromatographic analysis is made by a single peak, and retention time is 10-30 min.

5. The polysaccharide composition according to claim 3, wherein the polysaccharide is singly composed of α-D-glucopyranosyl, and the polysaccharide has an α-configuration and a connection manner of 1→4.

6. The polysaccharide composition according to claim 3, further comprising a fluorescence labeled product, a carboxymethylation product, a hydroxymethylation product, a hydroxypropylation product, an ethylene glycol product, a propylene glycol product or a polyethylene glycol product of the polysaccharide.

* * * * *